United States Patent [19]

Bolduc et al.

[11] Patent Number: 5,527,335
[45] Date of Patent: Jun. 18, 1996

[54] RETRACTING TIP TROCAR WITH PLUNGER SENSOR

[75] Inventors: Lee R. Bolduc, Foster City; Bryan E. Loomas, Santa Clara; Scott H. Miller, Sunnyvale, all of Calif.

[73] Assignee: Origin Medsystem, Inc., Menlo Park, Calif.

[21] Appl. No.: 335,597

[22] Filed: Nov. 8, 1994

Related U.S. Application Data

[63] Continuation of Ser. No. 69,179, May 28, 1993, abandoned.

[51] Int. Cl.$^6$ .................................................. A61B 17/34
[52] U.S. Cl. ............................................ 606/185; 604/164
[58] Field of Search .......................... 606/185; 604/164, 604/166, 272, 264, 26

[56] References Cited

U.S. PATENT DOCUMENTS

| | | | |
|---|---|---|---|
| 4,256,119 | 3/1981 | Gauthier | 128/754 |
| 4,535,773 | 8/1985 | Yoon | 604/51 |
| 4,601,710 | 7/1986 | Moll | 604/165 |
| 4,654,030 | 3/1987 | Moll et al. | 604/165 |
| 4,747,831 | 5/1988 | Kulli | 604/110 |
| 5,066,288 | 11/1991 | Deniega et al. | 604/274 |
| 5,104,382 | 4/1992 | Brinkerhoff et al. | 604/165 |
| 5,116,353 | 5/1992 | Green | 606/184 |
| 5,152,754 | 10/1992 | Plyley et al. | 604/164 |
| 5,158,552 | 10/1992 | Borgia et al. | 604/165 |
| 5,246,425 | 9/1993 | Hunsberger et al. | 604/272 X |
| 5,248,298 | 9/1993 | Bedi et al. | 604/264 X |
| 5,275,583 | 1/1994 | Crainich | 604/164 X |

FOREIGN PATENT DOCUMENTS

| | | | |
|---|---|---|---|
| 049522633 | 7/1992 | European Pat. Off. | A61B 17/34 |
| WOA9304716 | 3/1993 | WIPO | A61M 5/178 |

*Primary Examiner*—Michael H. Thaler
*Attorney, Agent, or Firm*—Limbach & Limbach

[57] ABSTRACT

A cannula is extended through the wall of a body cavity by a trocar having a piercing head slidable through the cannula between a condition extending distally from the cannula and a condition retracted within the cannula. A latch releasably secures the piercing head in the extended condition against the force of a spring which normally biases the piercing head to the retracted condition. Resiliently biased plungers extend longitudinally of the piercing head for retraction in response to counterforce as the piercing head advances through the wall of a body passage and extension upon the release of the counterforce. Extension of the plungers upon release of the counterforce functions to release the piercing head for retraction.

19 Claims, 6 Drawing Sheets

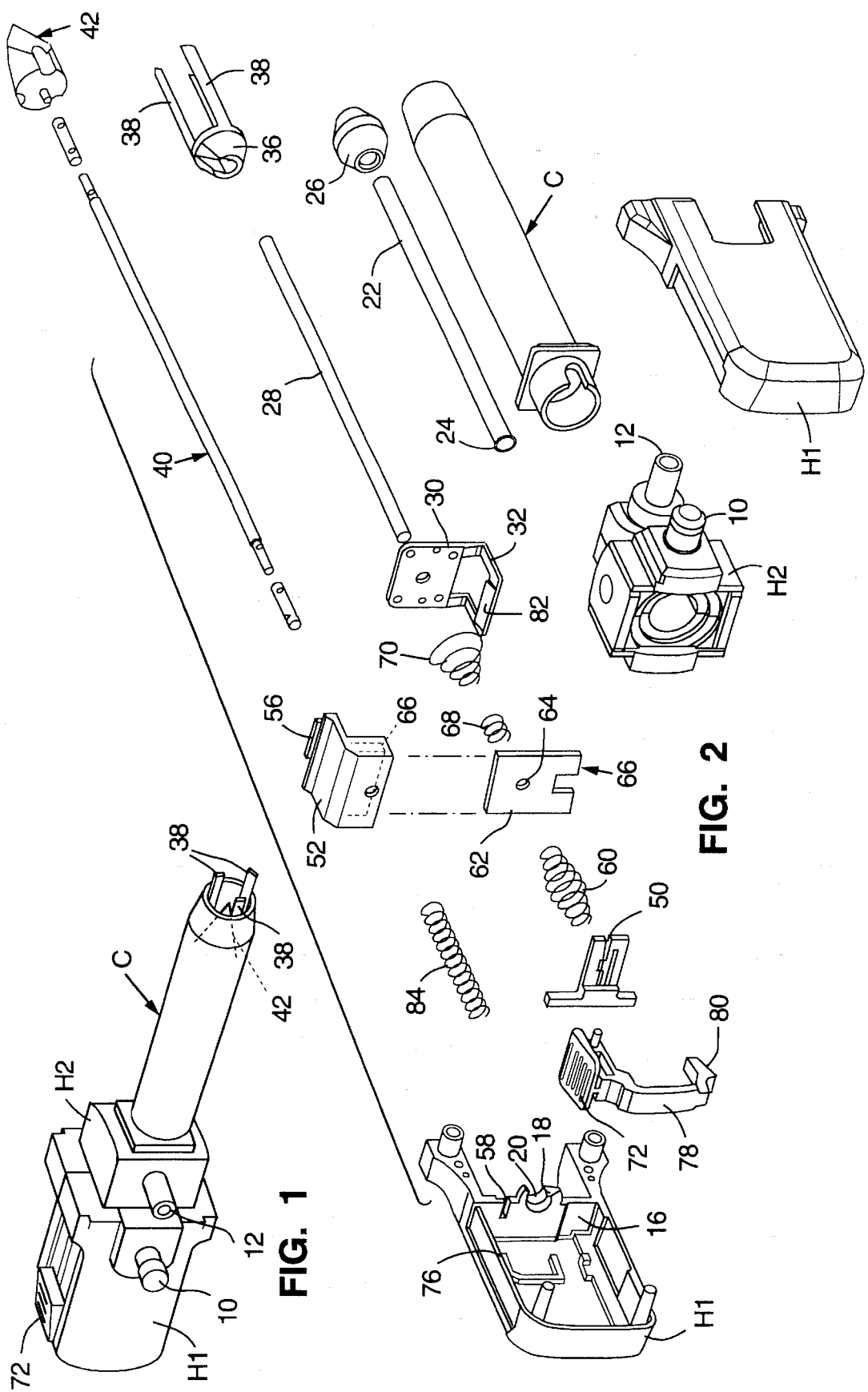

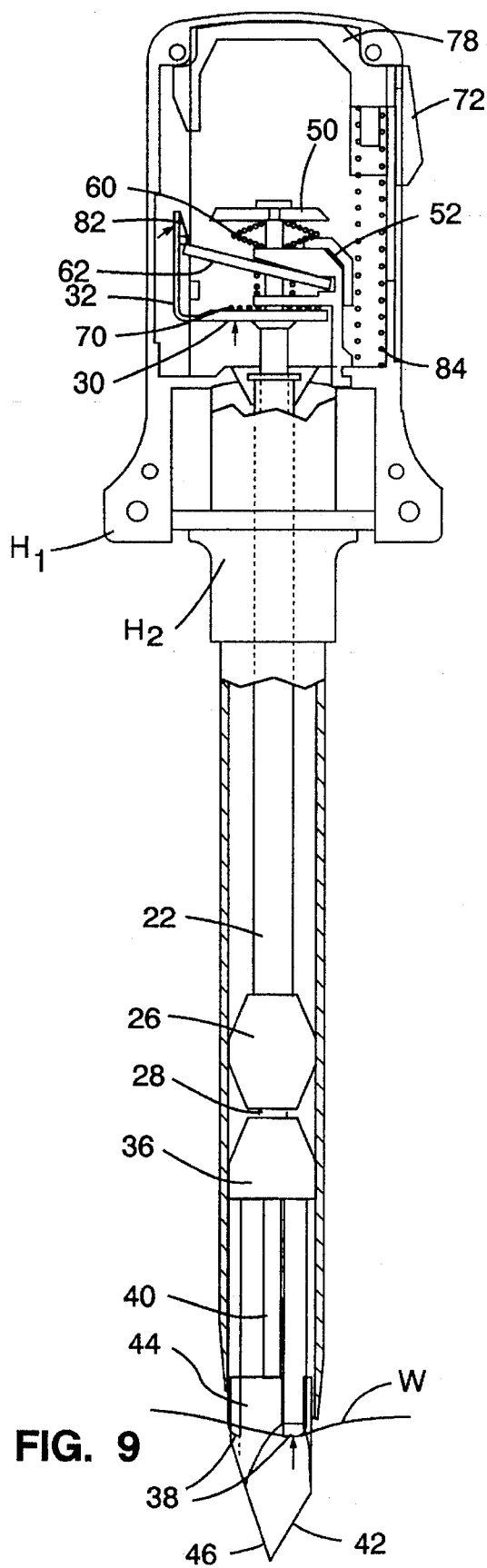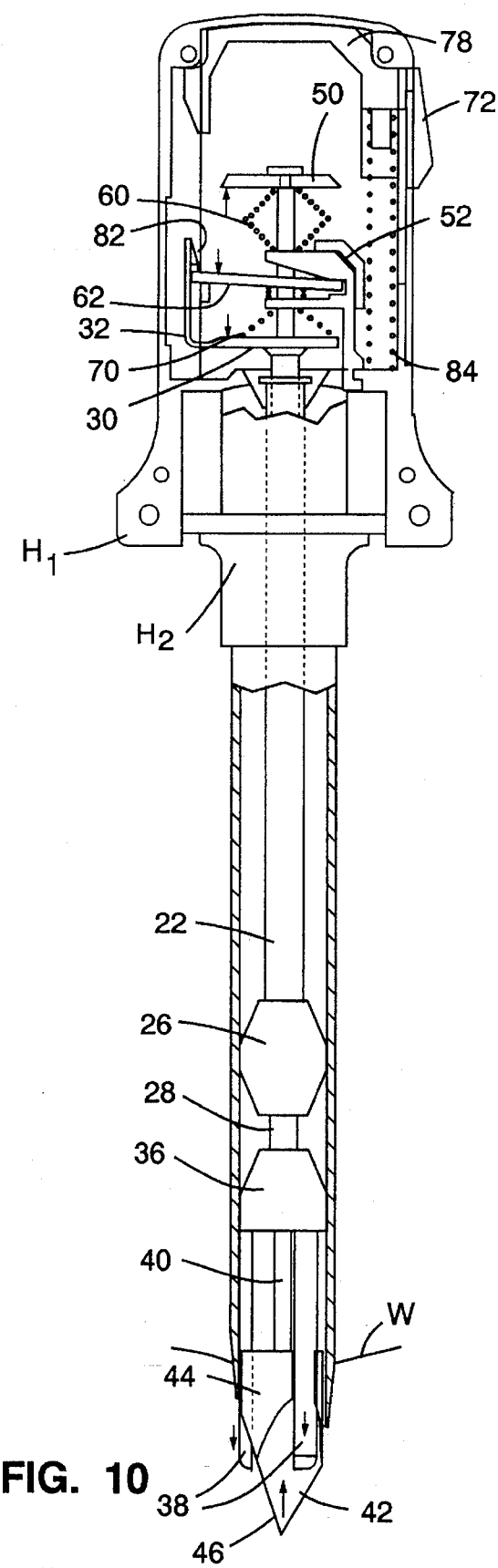

RETRACTING TIP TROCAR WITH PLUNGER SENSOR

This is a continuation of application Ser. No. 08/069,179 filed on May 28, 1993 now abandoned.

BACKGROUND OF THE INVENTION

The present invention relates to a surgical trocar for use in extending a cannula through the wall of a body cavity. In its more particular aspects, the invention is directed to a safety trocar having a piercing tip which extends distally from the cannula for purposes of forming a puncture in the wall and which, upon completion of the puncture, retracts into the cannula. The invention is especially concerned with an improved mechanism for sensing when the puncture is complete and triggering retraction of the piercing tip in response to this sensed condition.

Trocars are pointed surgical instruments which puncture tissue to obtain access to body cavities. Inherent with such instruments is the danger that after the intended puncture, the trocar will inadvertently puncture unintended tissue, vessels or organs.

The prior art teaches various techniques for providing needles and trocars with means to avoid inadvertent puncturing. For example, hollow Veress needles are provided with spring-loaded internal pins which pop out beyond the sharp cutting end of the needles after the intended puncture has been completed. U.S. Pat. Nos. 4,601,710 and 4,654,030 show trocars having shields in the form of a sleeve which extends around the point of the trocar after piercing is complete. The sleeves of the latter patents are received between the cannula being placed and the piercing point and, necessarily reduce the size of the piercing point which can be used with a cannula of a given diameter.

U.S. Pat. No. 4,535,773 teaches techniques for shielding the sharp tip of a trocar through either the interposition of an extendable shielding sleeve, or the retraction of the trocar into the trocar tube. The latter arrangement is seen in the embodiment of FIGS. 34 and 35 of the patent. It relies upon a solenoid operated detent which holds the trocar in the extended position relative to the cannula being placed and requires electronic sensing means in the piercing tip of the trocar to activate the detent for release.

More recent retracting tip trocars are found in U.S. Pat. Nos. 5,116,353, 5,152,754 and 5,158,552. The devices of the '353 and '552 patents employ movable piercing tips which retract partially during the piercing operation and, upon the completion of piercing, release for momentary distal movement and then retract fully into a shielded condition within the cannula. The device of the '754 patent employs a protective sleeve which extends through the cannula and is concentrically received around the piercing tip for partial retraction during the piercing operation. With the device of the latter patent, the sleeve retracts relative to the piercing tip in response to drag from the wall of the body cavity as the tip is advanced through the wall. Upon completion of the piercing function, the sleeve advances distally relative to the piercing tip to trigger retraction of the tip into the cannula.

The piercing tips in the devices of U.S. Pat. Nos. 5,116,353 and 5,158,552 "float" backwardly during the initial piercing operation and, upon completion of the operation, momentarily extend distally. This operation necessarily results in a tactile feel which is different than that which occurs in trocars wherein the piercing tip remains fixed during puncturing. It also, necessarily, requires that there be some extension of the piercing tip upon completion of the puncture. The device of U.S. Pat. No. 5,152,754 requires a shielding sleeve concentrically interposed between the piercing tip and the cannula being placed. The presence of this sleeve, necessarily, results in an increase in penetration force for a cannula of a given diameter.

It is desirable to minimize penetration force to enhance safety. For a given size cannula, penetration force can be reduced by maximizing penetrating head, or tip, size relative to the inner diameter of the cannula. This produces a larger cut upon penetration, thereby minimizing tissue dilation required to insert the cannula. Typically, the penetration force of existing devices is not optimized due to design constraints.

SUMMARY OF THE INVENTION

In its broadest aspects, the present invention provides a trocar for extending a cannula through the wall of a body cavity through means of a piercing tip which is slidably received within the cannula for movement between a condition extending distally from the cannula and a condition retracted within the cannula. The piercing head is normally biased toward the retracted condition. A latch plate releasably secures the head in the extended condition and, upon completion of the piercing function, a plunger carried by the piercing head extends to release the head for movement to the retracted condition.

In the preferred embodiment, the piercing head is carried by a trocar shaft which extends through the cannula and the latch comprises an apertured plate through which the rod extends. The plate is moveable between a condition wherein it binds upon the shaft to lock the tip in the extended condition and an aligned condition wherein it releases the shaft for retraction of the tip.

A principal object of the present invention is to provide a better, safer, faster retractable tip safety trocar.

Another object of the present invention is to provide a simplified retractable tip safety trocar that is easy to manufacture and has few component parts.

Another object of the invention is to provide such a trocar which is not dependent upon the piercing tip floating to a partially compressed state during piercing.

Still another object of the invention is to provide such trocar which does not embody a protective sleeve interposed between the piercing tip and the cannula within which the tip is received.

Still another object related to the latter object is to provide such a trocar wherein the diameter of the piercing tip for a given cannula is not reduced by the thickness of a protective sleeve.

A further object of the invention is to provide a trocar having reduced penetration force resulting from maximizing the penetration head, or tip, size relative to a given size cannula.

Yet another object of the invention is to provide such a trocar having a simplified latch comprising an apertured plate through which the trocar shaft extends which may be moved between cocked and aligned conditions with respect to the trocar shaft to selectively bind on the shaft, or release the shaft.

Another and more specific object of the invention is to provide such a trocar which employs plungers extending slidably around the piercing tip to sense when piercing is complete and trigger retraction of the tip in response to such sensing.

Yet another object of the invention is to provide such a trocar in which the tip retracts quickly by virtue of not having to first advance to trigger retraction.

Another object of the invention is to provide such a trocar wherein sensing for retraction occurs at the outer diameter of he piercing tip, thereby most accurately sensing and triggering in response to completion of a puncture.

These and other objects will become more apparent when viewed in light of the following detailed description and accompanying drawings.

BRIEF DESCRIPTION OF THE DRAWINGS

FIG. 1 is a perspective view of the inventive trocar and the cannula employed therewith, with the piercing tip shown in the retracted condition;

FIG. 2 is an exploded perspective view of the trocar;

FIG. 5 is an end view of the trocar taken from the bottom of FIG. 4; and

FIGS. 6, 7, 8, 9 and 10 are cross-sectional elevational views diagrammatically illustrating the trocar through the steps of being armed for piercing, loaded during piercing, and retracting at the culmination of piercing.

DESCRIPTION OF THE PREFERRED EMBODIMENT

The trocar is designated by its entirety by the letter "T" and shown cooperating with a cannula "C". The cannula has a lumen "L" extending fully therethrough. A housing $H_1$ forms part of the proximal portion of the trocar and confines its latching mechanism. A housing $H_2$ is fixedly secured to the proximal end of the cannula "C" and proportioned to releasably mate with the housing $H_1$ as shown in FIG. 4.

Figure 3:
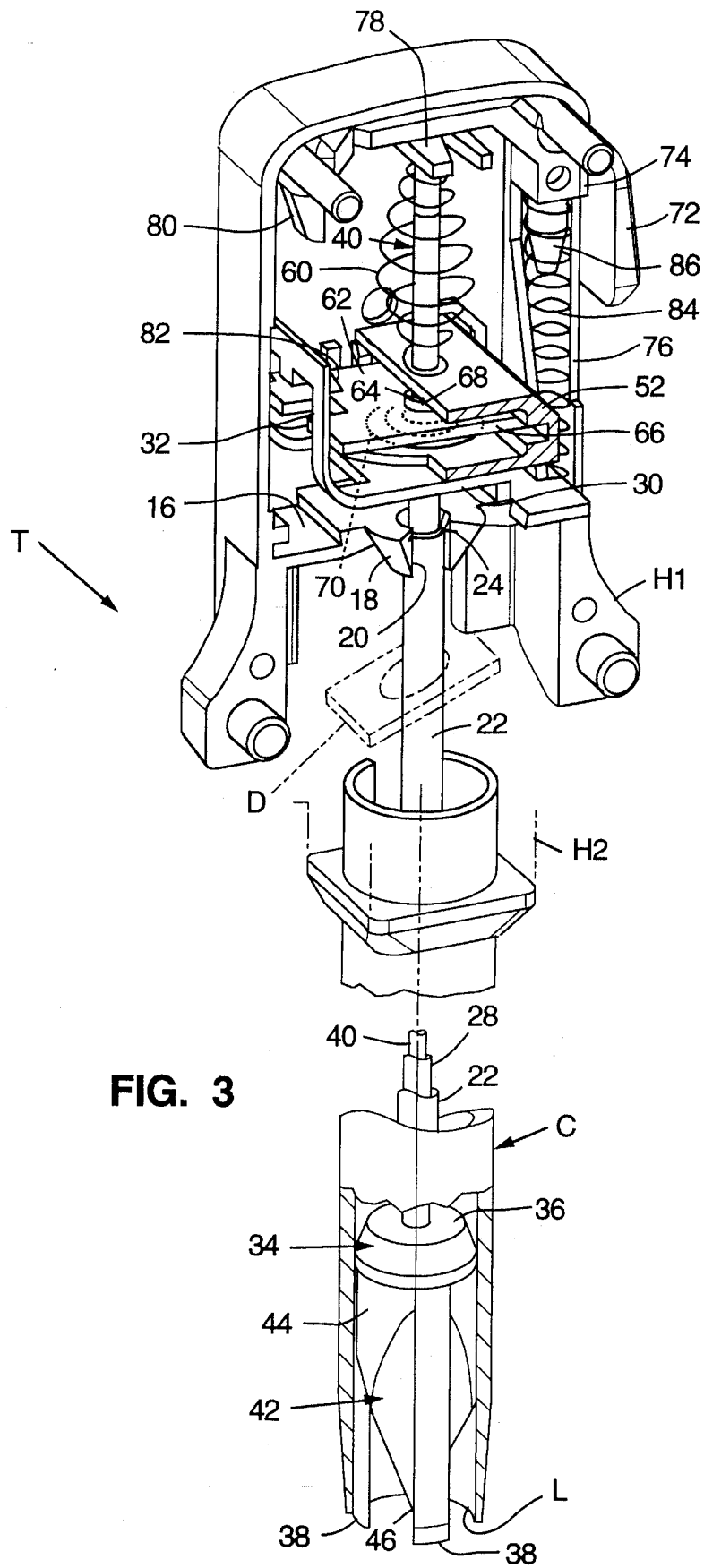
FIG. 3 is a perspective view of the trocar, with the piercing tip retracted and one side of the housing removed to expose the interior.
Figure 4:
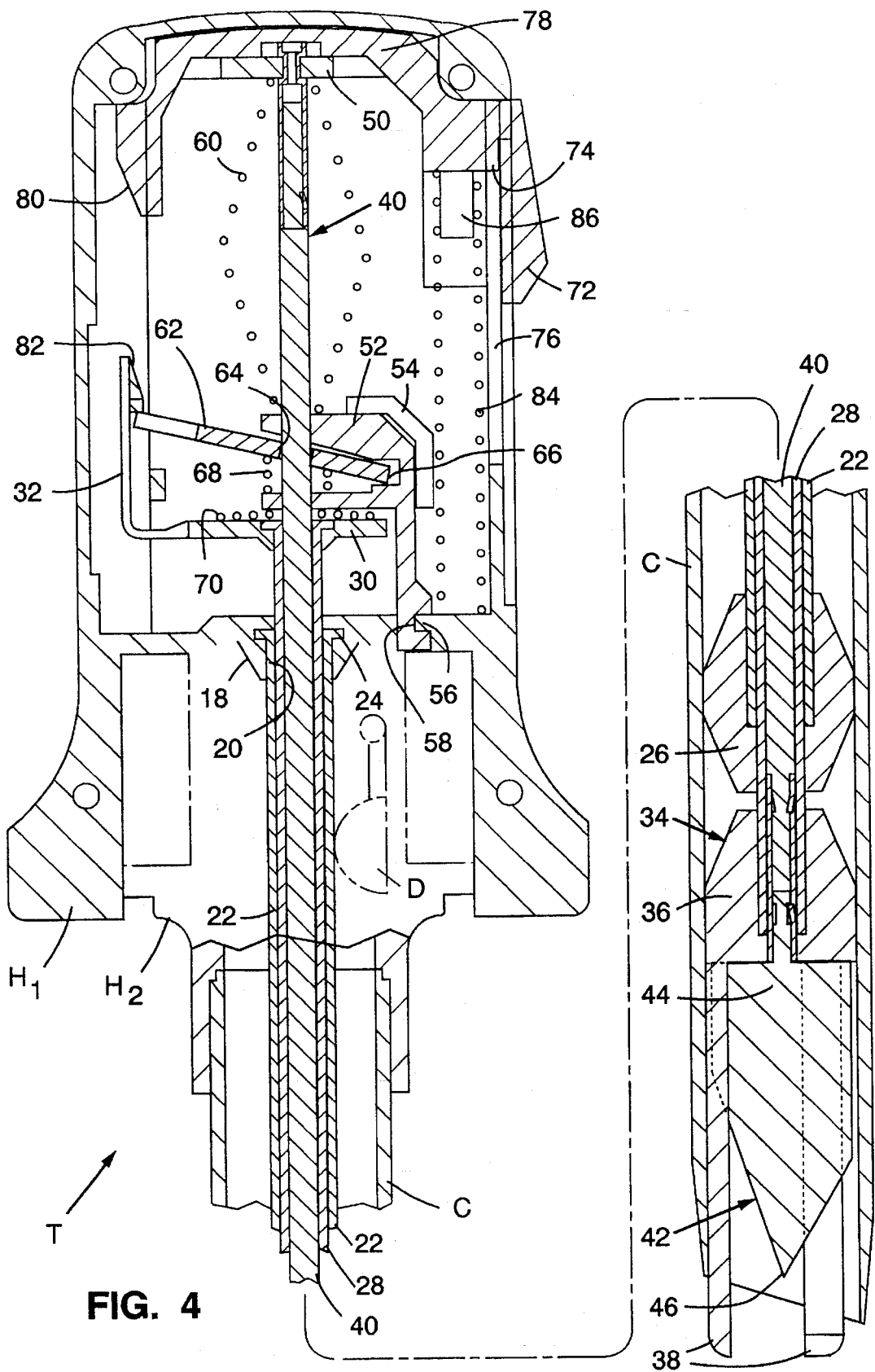
FIG. 4 is an elevational view of the trocar with the piercing tip in the retracted condition and one side of the housing for the latch mechanism removed.

During the course of extending the cannula through the wall of a body cavity, the housings $H_1$ and $H_2$ are assembled in the mated condition shown in FIG. 4. Once the cannula is extended through the wall of the cavity, the housing $H_1$ and the trocar components which it carries may be removed from the housing $H_2$, leaving the cannula in place within a puncture extending through the wall. A spring biased valve door "D" closes against the annular seal of the cannula upon removal of the housing $H_1$ from the housing $H_2$. The door may be selectively opened by a push-button 10 which engages a lever secured to the valve door. As shown, a gas entry port 12 is also provided on the housing $H_2$ to provide for the flow of gas to and from the lumen L.

The housing $H_1$ is formed with a proximal end wall 16 having a centrally disposed boss 18 extending therefrom. An opening 20 extends through the boss. A tube 22 is captured in the opening 20 by a flared upper end 24 formed on the tube and received within a groove in the boss 18. The latter connection secures the tube 24 against axial movement relative to the housing $H_1$, while permitting the tube to rotate about its longitudinal axis relative to the housing. The lower end of the tube 22 carries a frusto-conical spacer 26 proportioned for close slidable receipt in the lumen L.

A plunger tube 28 is slidably disposed within the tube 22 and extends from either end thereof. The upper end of the tube 28 is fixedly secured to a latch 30 formed with a resilient spring arm 32 on one end thereof. The lower end of the tube 28 carries a plunger 34 having a base portion 36 secured to the tube 28 for rotation about the axis of the tube and against axial movement relative to the tube. Three plunger fingers 38 extend distally from the base portion at equally spaced circumferential positions. The outer surfaces of fingers 38 are formed to slide on the inside surface of the lumen L and are of a shape complemental to the surface L. A trocar shaft 40 extends slidably through the plunger tube 28 for axial movement relative thereto. The lower end of the shaft 40 carries a piercing head 42 slidably received within the lumen L. The proximal portion 44 of the piercing edge is of a cylindrical configuration having a diameter closely approximating that of the lumen L. The distal end, designated 46, of the piercing head 42 is pointed and, in the preferred embodiment, formed with three facets (see FIG. 5). Grooves 48, having a semi-cylindrical, elliptical, rectangular, triangular or other shape, are formed in the proximal portion 44 for slidable receipt of the plunger fingers 38. From FIG. 5 it will be seen that the grooves 48 are formed so as to be disposed centrally of the facets of the piercing head. The inside surfaces of the fingers 38 are of a configuration complimenting that of the grooves 48.

The piercing head 42 is secured against axial movement relative to the shaft 40, while at the same time being free to rotate about the axis of the shaft. Likewise, the plunger 34 is secured against axial movement relative to the plunger tube 28, while being free to rotate around its axis. This interrelationship leaves the plunger 34 and the piercing head 42 free to rotate relative to one another and avoids any binding which might result from the fingers 38 being askew relative to the grooves 48.

The upper end of the trocar shaft 40 is fixedly secured to a spring keeper 50. A flat surface on the shaft engages a slot in the keeper to secure the shaft against rotation about the axis of the shaft. Intermediate the latch 30 and the keeper 50 the shaft 40 extends through a fixed bearing block 52 for free axial movement relative to the block. The block is of generally U-shaped configuration (see FIG. 4) with the sides closed to prevent the legs of the U from deflecting. The block 52 is fixed relative to the housing $H_1$ by a partial channel 54 formed on the housing $H_1$ and extending partially around one side of the block. A groove 56 formed on the block 52 also engages within a slot 58 formed in the housing $H_1$ to secure the block against movement relative to the housing.

A compression coil spring 60 is concentrically received around the trocar shaft 40 between the keeper 50 and the bearing block 52. This spring functions to normally bias the trocar shaft to the retracted "at rest" condition shown in FIG. 4. A latch plate 62 having an opening 64 extending therethrough for a slidable receipt of the shaft 40 is disposed within the bearing block for up and down movement relative thereto (as viewed in FIG. 4). Opening 64 is illustrated as cylindrical, but could be a slot or other configuration. One end of the latch plate 62 is loosely confined within a groove 66 formed in the bearing block. Through this loose interrelationship, the bearing block effectively functions to pivotally support the end of the plate received within the groove. The other end of the plate 62 is free to move up and down.

The material and dimensions of the trocar shaft 40 and the latch plate 62 may vary. In one example, the plate and shaft are fabricated of stainless steel, with the shaft having a diameter of 0.090 inches and the opening 64 in the plate having a diameter of 0.095 inches.

Figure 7:
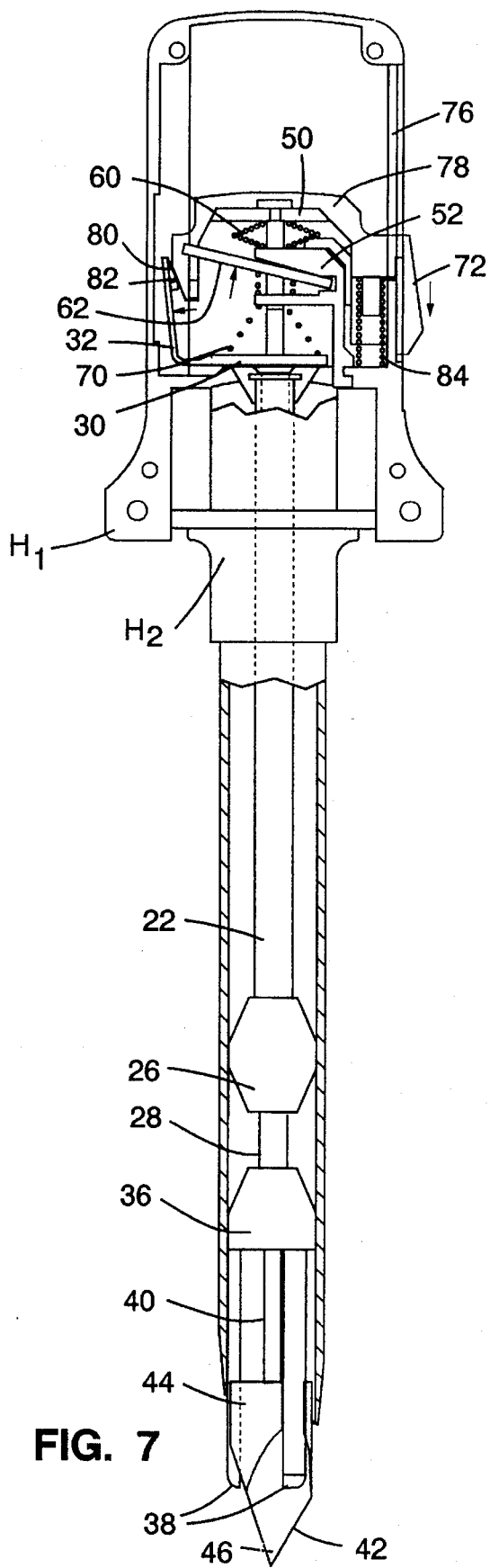

When cocked relative to the shaft as shown in FIG. 7, the opening 64 in the plate binds on the shaft 40 to lock the shaft against axial movement. A coil spring 68 (see FIG. 4) is loosely received around the shaft 40 in interposed condition between the plate 62 and the inside of the block 52 to normally bias the plate to the cocked condition shown in FIG. 7.

A helical compression coil spring 70 is loosely received around the shaft 40 between the latch 30 and the bearing block 52. The latter spring functions to normally bias the latch downwardly (as viewed in FIG. 4) relative to the bearing block. Its helical configuration enables the spring to be compressed to the generally flat condition shown in FIG. 4.

The housing $H_1$ also carries a button 72 having a boss 74 slidably received within a slot 76 formed within the housing. The button 72 is integral with the boss 74 and a bridge 78 which extends over the top of the keeper 50 to the inside of the housing $H_1$. The end of the bridge opposite the button 72 is formed with a wedge 80 disposed for camming engagement with a wedge 82 carried by the spring arm 32. A spring 84, formed as a compression spring, extension spring, or other suitable alternative, is received around a pin 86 integral with the bridge 78 and normally functions to bias the button proximally (upwardly as viewed in FIG. 4) relative to the housing $H_1$.

OPERATION

FIG. 4 illustrates the trocar in the at rest condition with the piercing point fully retracted. As there seen, the trocar shaft 40 is fully retracted by the spring 60 and the plunger is retracted by virtue of the top surface of the piercing head 42 pushing on the base portion 36 of the plunger 34. The plate 62 is biased by the partially compressed spring 68 and the spring 70 is fully compressed. The spring 84 is biased to hold the button 86 in the fully retracted proximal position.

Figures 5, 6:
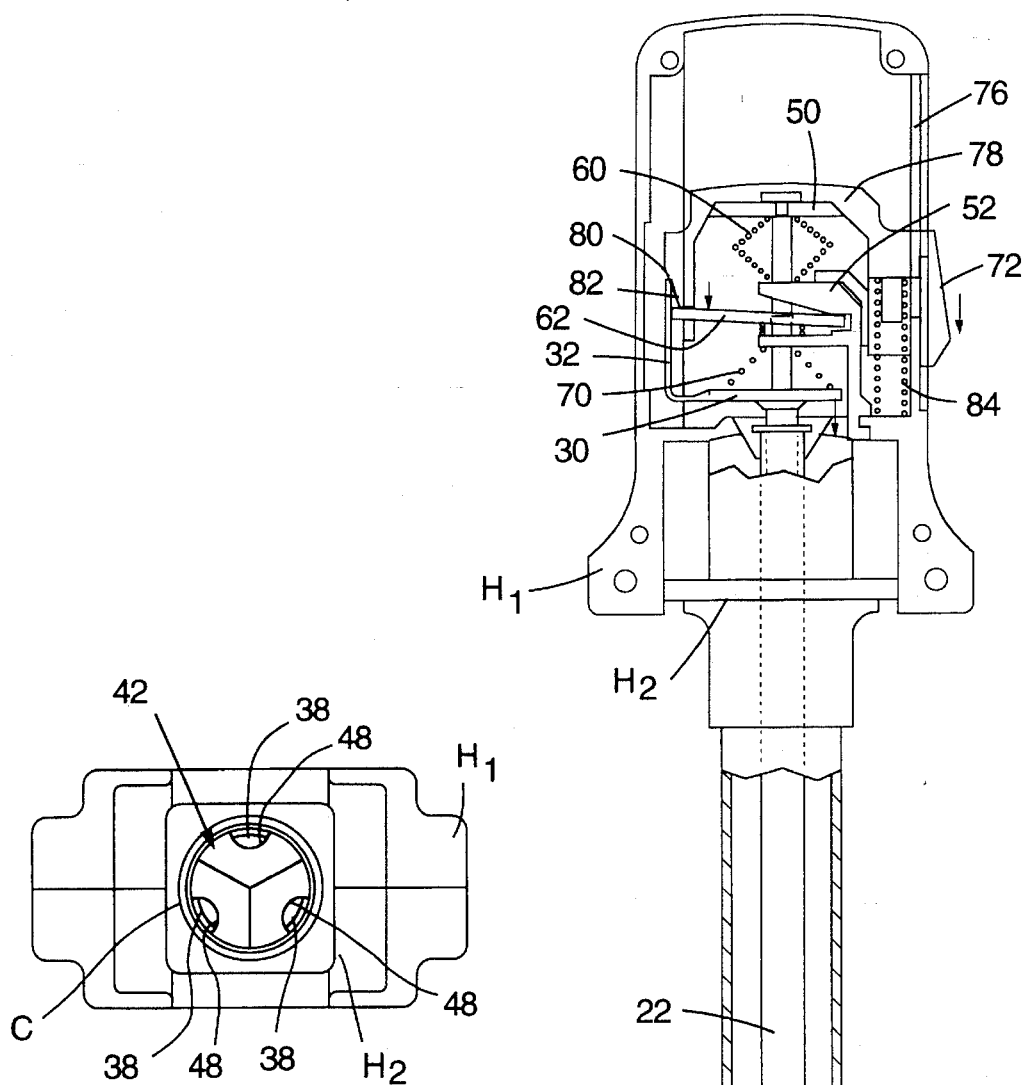
Figure 8:
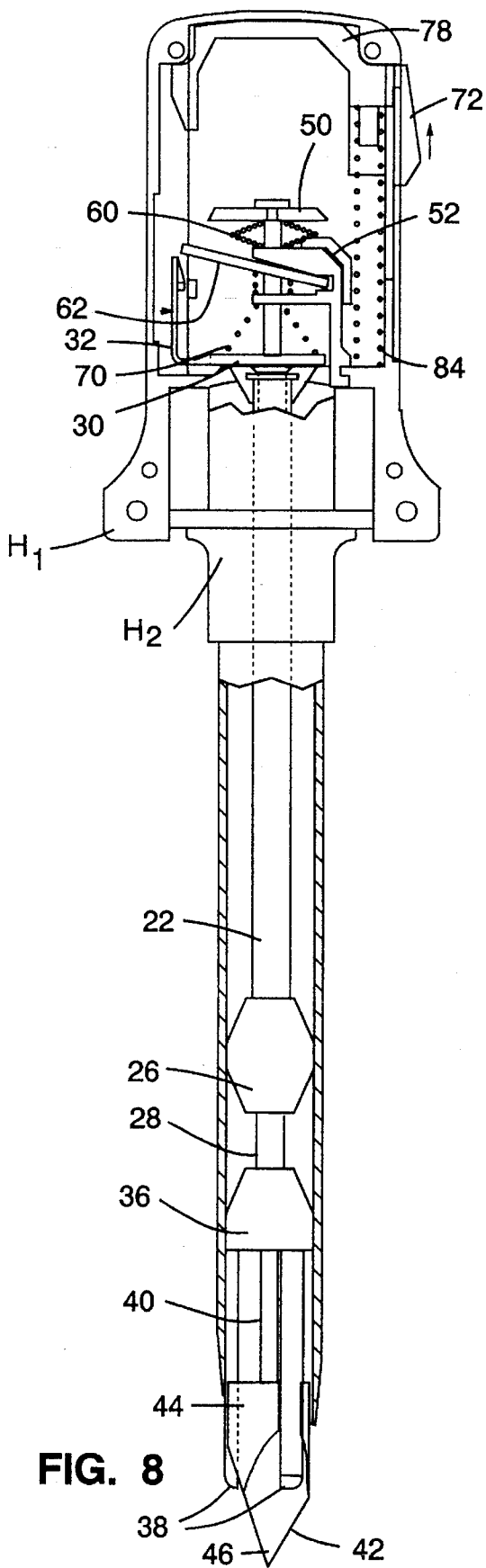

FIG. 6 shows the trocar just prior to being fully armed. As there shown, the button 72 is being pushed downwardly against the force of the spring 84 and the bridge 78 is pushing down on the spring keeper 50, compressing spring 60, to extend the piercing head 42 distally. If any space exists between the under surface of the wedge 82 and the top surface of the plate 66, this space is taken up as the latch 30 moves downward with the piercing head 42 under the influence of the spring 70. Continued movement of the button brings the ramp 80 into the camming engagement with the ramp 82 to force the spring arm laterally beyond the distal end of the plate 62 and release the plate for upward swinging movement to the cocked locking condition responsive to the spring 68. The latter operation occurs when the button 72 is pushed to its distal extreme as shown in FIG. 7. Once in this condition, the opening 64 and the latch plate 62 binds against the trocar shaft 40 to lock the shaft in the fully extended condition. Thereafter, the button 72 may be released as shown in FIG. 8 to return to its retracted proximal condition without altering the cocked condition of the trocar. Full extension of the piercing point also permits the plunger to move to the fully extended distal position under the influence of the spring 70. As so conditioned, the fingers of the plunger extend slightly beyond the faceted surfaces at the distal point of the piercing head. The latter condition may also be seen in FIGS. 7 and 8.

FIG. 9 shows a trocar in the loaded condition which occurs as the piercing point is pushed through the wall "W" of a body cavity. During this operation, the plunger fingers 38 are pushed proximally back to the point where the ramp 82 on the latch 30 snaps past and over the top of the latch plate 62. As so conditioned, the latch plate remains in the cocked condition binding the trocar shaft to maintain the piercing point fully distally extended. As piercing is completed, however, the fingers penetrate the puncture formed by the point. Then, under the influence of the spring 70, the latch plate is forced to the generally horizontal condition, thus releasing the trocar shaft for retraction by the spring 60. Such retraction returns the trocar to the at rest condition shown in FIG. 4. As so conditioned, the top surface of the piercing head 42 engages the bottom surface of the plunger base portion 36 to lift the latch 30 upwardly or proximally against the force of the springs 70.

FIG. 4 shows how the distal ends of the plunger fingers 38 are outwardly rounded. Alternatively, the distal ends of fingers 38 can be frustro-conical, spherical, beveled, or otherwise blunted in shape. This configuration facilitates extension of the fingers through a puncture formed by the piercing head and also avoids the possibility that the ends of the fingers might cut into the tissue being pierced by the piercing head. During the piercing operation, a counterforce is exerted on the ends of the plunger fingers by the tissue of the wall being pierced. This counterforce or drag is what forces the plunger to the proximal retracted condition shown in FIG. 9.

Immediately upon completion of the piercing function, the piercing head retracts to the at rest condition fully confined within the cannula. As so positioned, the head is isolated from the possibility that it will inadvertently puncture unintended tissue, vessels or organs.

Once the puncture is complete, the cannula may be further advanced into the body cavity through the puncture. The housing $H_1$ may then be removed from the housing $H_1$, thus withdrawing the full puncturing mechanism and leaving the cannula in place in the puncture.

CONCLUSION

The present invention provides a safety trocar for placement in the lumen of an cannula to insert the cannula through the wall of a body cavity. In operation, the piercing point of the trocar is initially distally extended from the end of the cannula. Upon completion of its piercing functions, fingers extend relative to the piercing head and trigger a mechanism which retracts the piercing head into the cannula to an isolated condition where it cannot inadvertently puncture unintended tissue, vessels or organs.

We claim:

1. A trocar for placement in the lumen of a cannula to insert the cannula through the wall of a body cavity, said trocar comprising:
    a) a piercing head slidable through the lumen of the cannula, said head having:
        1) a proximal end portion having an arcuate surface of a diameter closely approximating that of the lumen;
        2) a pointed distal end portion for piercing the wall of the body cavity; and,
        3) at least one groove formed in the arcuate surface and extending longitudinally fully across the proximal end portion;
    b) a shaft secured to the proximal end of the piercing head for extension through the cannula;
    c) a plunger extending longitudinally through the groove and fully across the proximal end portion of the piercing head, said plunger being proportioned for close slidable receipt within the groove and being extendable beyond the proximal end portion in the direction of distal end portion;

d) extension means secured to the shaft to selectively maintain the piercing head in a condition with the distal end portion extended from the cannula; and, e) retraction means operatively associated with the plunger and the extension means to effect movement of the piercing head from the condition where the distal end portion is extended from the cannula to a condition where the distal end portion is confined within the cannula in response to movement of the plunger in the direction of the distal end portion.

2. A trocar according to claim 1 wherein:

a) a plurality of grooves are formed in the arcuate surface and extend longitudinally fully across the proximal end portion at circumferentially spaced locations; and, b) the plunger includes portions extending through each of the grooves and fully across the proximal end portion for extension beyond the proximal portion end in the direction of the distal end portion.

3. A trocar according to claim 1 wherein the proximal end portion of the piercing head has a cylindrical outer surface complemental to the lumen of the cannula and the plunger has a cylindrical outer surface contiguous with that of the proximal end portion.

4. A trocar according to claim 1 wherein:

a) the plunger is longitudinally moveable relative to the piercing head and may retract proximally relative to the head in response to drag from the wall of the body cavity as the head is advanced through the wall; and b) biasing means is provided to advance the plunger distally after the piercing head has penetrated through the wall of the body cavity.

5. A trocar for placement in the lumen of a cannula to insert the cannula through the wall of a body cavity, said trocar comprising:

a) a housing;

b) a shaft carried by the housing and having a piercing head slidable through the lumen of the cannula, said head having:

1) a proximal end portion having an arcuate surface of a diameter closely approximating that of the lumen;

2) a pointed distal end portion for piercing the wall of the body cavity; and, 3) at least one groove formed in the arcuate surface and extending longitudinally fully across the proximal end portion;

c) a plunger extending longitudinally through the groove and fully across the proximal end portion of the piercing head, said plunger being proportioned for close slidable receipt within the groove and being extendable beyond the proximal end portion in the direction of the distal end portion; and, d) means for retracting the shaft proximally relative to the housing after the piercing head has penetrated through the wall of the body cavity, said means operating in response to movement of the plunger distally relative to the housing.

6. A trocar according to claim 5 further comprising means for advancing the plunger distally relative to the shaft after the distal end portion has penetrated through the wall of the body cavity and means for triggering the retracting means upon distal advancement of the plunger.

7. A trocar according to claim 5 wherein:

a) a plurality of grooves are formed in the arcuate surface and extend longitudinally fully across the proximal end portion at circumferentially spaced locations; and, b) the plunger includes portions extending through one or more of the grooves and fully across the proximal end portion for extension beyond the proximal end portion in the direction of the distal end portion.

8. A trocar according to claim 5 wherein the proximal end portion of the piercing head has a cylindrical outer surface complemental to the lumen of the cannula and the plunger has a cylindrical outer surface contiguous with that of the proximal end portion.

9. A trocar according to claim 5 wherein:

a) the plunger is longitudinally moveable relative to the shaft and may retract proximally relative to the piercing head in response to drag from the wall of the body cavity as the trocar is advanced through the wall; and, b) biasing means is provided to advance the plunger distally after the piercing head has penetrated through the wall of the body cavity.

10. A trocar for placement in the lumen of a cannula to insert the cannula through the wall of a body cavity, said trocar comprising:

a) a housing;

b) a shaft carried by the housing and having a piercing head slidable through the lumen of the cannula, said head having:

1) a proximal end portion having an arcuate surface of a diameter closely approximating that of the lumen;

2) a pointed distal end portion for piercing the wall of the body cavity; and, 3) at least one groove formed in the arcuate surface and extending longitudinally fully across the proximal end portion;

c) a plunger extending longitudinally through the groove and fully across the proximal end portion of the piercing head, said plunger being proportioned for close slidable receipt within the groove;

d) means resiliently biasing the plunger to enable said plunger to retract relative to the piercing head in response to drag from the wall of a body cavity as the piercing head advances through the wall of the body cavity and to advance the plunger distally after the piercing head has penetrated the wall of the body cavity; and, e) means for retracting the shaft proximally relative to the housing after the piercing head has penetrated through the wall of the body cavity, said means operating in response to movement of the plunger distally relative to the housing.

11. A trocar according to claim 10 wherein:

a) a plurality of grooves are formed in the arcuate surface and extend longitudinally fully across the proximal end portion at circumferentially spaced locations; and, b) the plunger includes portions extending through each of the grooves for extension beyond the proximal end portion in the direction of the distal end portion.

12. A trocar according to claim 10 wherein the proximal end portion of the piercing head has a cylindrical outer surface complemental to the lumen of the cannula and the plunger has a cylindrical outer surface contiguous with that of the proximal end portion.

13. A trocar for placement in the lumen of a cannula to insert the cannula through the wall of a body cavity, said trocar comprising:

a) a shaft slidable through the lumen of the cannula, said shaft having a distal piercing head;

b) retention means to releasably maintain the shaft within the cannula in a condition with the piercing head extending distally of the cannula;

c) a plunger mounted for longitudinal movement relative to the shaft, said plunger being retractable relative to the piercing head in response to resistance from the wall of the body cavity as the piercing head is advancing through the wall;

d) means biasing the plunger for distal extension relative to piercing head as the shaft passes fully through the wall;

e) a spring biasing the shaft for retraction into the cannula;

f) a movable plate having an opening through which the shaft extends; and, g) means responsive to distal extension of the plunger to move the plate from a cocked condition wherein the opening binds the shaft against movement to an aligned condition releasing the shaft for movement to enable the spring to retract the shaft into the cannula.

14. A trocar for extending a cannula having a lumen through the wall of a body cavity, said trocar comprising:

a) a piercing head slidable through the lumen of the cannula between a condition extending distally from the cannula and a condition retracted within the cannula, said head having a sharpened distal portion, a proximal portion with unsharpened surfaces complemental to the lumen of the cannula and a groove extending longitudinally fully across the proximal portion;

b) a latch releasably securing the piercing head in the extended condition against the force of a spring which normally biases the piercing head to the retracted condition;

c) a plunger extending longitudinally through the groove and fully across the proximal portion of the piercing head for retraction in response to counterforce as the piercing head advances through the wall of a body passage and extension upon the release of the counterforce;

d) means resiliently biasing the plunger for distal extension relative to the piercing head upon release of the counterforce; and, e) retraction means releasing the piercing head for retraction upon extension of the plunger in response to release of the counterforce.

15. A trocar according to claim 14 wherein:

a) a plurality of grooves extend longitudinally fully across the proximal end portion of the piercing head at circumferentially spaced locations; and, b) the plunger includes portions extending slidably through one or more of the grooves and fully across the proximal end portion of the piercing head.

16. A trocar according to claim 14 wherein:

a) the plunger is slidably received in the groove extending longitudinally fully across the unsharpened surfaces of the proximal portion; and, b) the plunger has an outer surface contiguous with the unsharpened surfaces of the proximal portion.

17. A trocar according to claim 14, wherein the plunger retracts in response to drag from the wall of a body cavity as the head advances through the wall and extends after the head has penetrated the wall.

18. A trocar according to claim 14, wherein;

a) a plurality of grooves extend longitudinally fully across the proximal portion of the head; and, b) the plunger includes portions extending slidably through each of the grooves.

19. A trocar for extending a cannula through the wall of a body cavity, said trocar comprising:

a) a piercing head slidable through the cannula between a condition extending distally from the cannula and a condition retracted within the cannula, said head being carried by a shaft extending through the cannula;

b) a spring normally biasing the piercing head to the retracted condition;

c) a plunger extending longitudinally of the piercing head for retraction in response to counterforce as the piercing head advances through the wall of a body passage and extension upon the release of the counterforce;

d) means resiliently biasing the plunger for distal extension relative to the piercing head upon release of the counterforce;

e) a movable plate having an opening through which the shaft extends, said plate being movable between a cocked condition wherein the opening binds the shaft to secure the piercing head in the extended condition and an aligned condition releasing the shaft for movement to enable the spring to retract the head into the cannula; and, f) means responsive to distal extension of the plunger to move the plate from the cocked condition to the aligned condition.

* * * * *